United States Patent [19]

Nomura et al.

[11] Patent Number: 4,571,423
[45] Date of Patent: Feb. 18, 1986

[54] SUBSTITUTED 5-AMINOMETHYL-2-ACYLAMINOPYRROLO[2,3-D]PYRIMIDIN-4-ONES

[75] Inventors: Hiroaki Nomura, Osaka; Hiroshi Akimoto, Hyogo, both of Japan

[73] Assignee: Takeda Chemical Industries Ltd., Osaka, Japan

[21] Appl. No.: 475,962

[22] Filed: Mar. 16, 1983

[30] Foreign Application Priority Data

Mar. 16, 1982 [JP] Japan .................................. 57-41910

[51] Int. Cl.$^4$ .................. C07D 487/04; C07D 413/06; A61K 31/505; A61K 27/00
[52] U.S. Cl. .................................... 544/280; 544/117
[58] Field of Search ................................ 544/280, 117

[56] References Cited

U.S. PATENT DOCUMENTS 4,435,569  3/1984  Nishimura et al. .................. 544/280

FOREIGN PATENT DOCUMENTS 075881   4/1983  European Pat. Off. ............ 544/280
079447   5/1983  European Pat. Off. ............ 544/280
185284  11/1982  Japan .................................. 544/280
812366   4/1959  United Kingdom ................ 544/280

OTHER PUBLICATIONS

March, J., "Advanced Organic Chemistry", pp. 820-823, McGraw-Hill Book Co., 2nd ed., (1977).
Duffy, T. D., et al., J. Chem. Soc. Perkin Trans. I, (16), pp. 1921-1929, (1974).
Seela, F., et al., Chem. Ber., 110, 1462-1469, (1977).

Primary Examiner—George F. Lesmes
Assistant Examiner—S. A. Gibson
Attorney, Agent, or Firm—Wegner & Bretschneider

[57] ABSTRACT

7-Deazapurine derivatives of the formula (I):

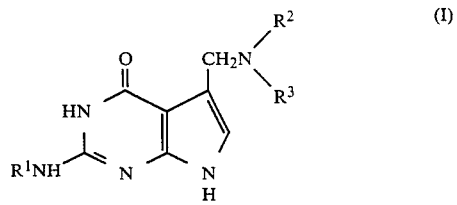

($R^1$ is an acyl group; each of $R^2$ and $R^3$ is an alkyl, alkenyl or aralkyl group of alternatively $R^2$ and $R^3$, taken together with the adjacent nitrogen atom, form a cyclic amino group, and each of said alkyl group, alkenyl group, aralkyl group and cyclic amino group has a methylene group in $\alpha$-position) and salts thereof are of value as intermediates for the production of antitumor agents, biological reagents, etc.

8 Claims, No Drawings

SUBSTITUTED 5-AMINOMETHYL-2-ACYLAMINOPYRROLO[2,3-D]PYRIMIDIN-4-ONES

This invention relates to a 7-deazapurine derivative of the formula (I):

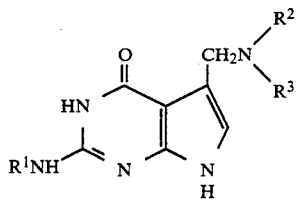

(R¹ is an acyl group; each of R² and R³ is an alkyl, alkenyl or aralkyl group or alternatively R² and R³, taken together with the adjacent nitrogen atom, form a cyclic amino group, and each of said alkyl group, alkenyl group, aralkyl group and cyclic amino group has a methylene group in α-position) or a salt thereof, which is of value as intermediate in the production of antitumor agents, biological reagents, etc. The invention also relates to a process for producing said 7-deazapurine derivative or a salt thereof.

The hypermodified bases, e.g. Q base (queuine) which have the same skeletal structure as the compound of this invention and which can be easily derived therefrom, as well as its analogs, are widely distributed in the natural kingdom, for example as constituent units of certain tRNAs (tRNA$^{Tyr}$, tRNA$^{His}$, tRNA$^{Asp}$ and tRNA$^{Asn}$). Generally, tRNAs recognize codons in mRNAs and in this sense are involved in the synthesis of proteins having specific amino acid sequences designated by genetic information. Q base and its related analogous bases are located at the position of the first position of anticodons in those tRNAs which correspond to the above four amino acids and thus have a significant influence upon the exact transfer of genetic information (translation process). Recent advances in research have revealed that the cancer cells, unlike normal cells, contain Q base-deficient tRNAs, which, upon administration of exogenous Q base, are converted to normal cell tRNAs.[1]

[1] Nishimura S., Metabolism Vol. 17, Feature Issue (Gan (cancer) '80), pp. 127–136 (1980).

There is also a report that based on the above facts, the Q base (i.e. queuine) has antitumor effect on certain experimental tumors.[2]

[2] J. R. Katze et al, Biochem. Biophys. Res. Comm. 96, 313 (1980).

However, Q base and its analog having such interesting medical, pharmacological and biological characteristics occur only in very minute quantities in natural materials and it has heretofore been impossible to obtain them in useful quantities. Recently, a chemical total synthesis of Q base and its analogs have been reported by Goto et al[3] but their process involves a time-consuming series of steps and is not fully satisfactory from commercial points of view.

[3] N. Okada et al., J. Biol. Chem. 254 3067 (1979)

After a thorough study, the present inventors have succeeded in synthesizing the 7-deazapurine derivatives of the general formula (I) and salts, and they have developed a completely new route for synthesis of Q base and its analogs involving the use of the new class of intermediates. It was found that the use of such an intermediate gave many advantages. For example, the whole process may start from an inexpensive material, involves fewer reaction steps, provides higher reaction yields and offers the ease of reaction procedures and treatments, making the process very suited for a large-scale production of Q base and its analogs. This invention is predicated on the above findings.

Refering to the above formula (I), the acyl group R¹ may for example be a $C_{1-18}$ alkanoyl group (e.g. formyl, acetyl, propionyl, butyryl, isobutyryl, valeryl, isovaleryl, pivaloyl, hexanoyl, heptanoyl, octanoyl, 2-ethylhexanoyl, nonanoyl, decanoyl, undecanoyl, tridecanoyl, tetradecanoyl, pentadecanoyl, hexadecanoyl, heptadecanoyl, octadecanoyl), or a $C_{7-12}$ aroyl group (e.g. benzoyl, toluoyl, naphthoyl), phenylacetyl, cinnamoyl or the like. Particularly preferred are $C_{1-10}$ alkanoyl groups, more preferably $C_{4-10}$ alkanoyl groups and benzoyl.

The groups R² and R³ may be the same group or different groups, and each of them has a methylene group in α-position. Examples of the alkyl group represented by R² and R³ include groups containing about 1 to 10 carbon atoms such as methyl, ethyl, propyl, butyl, isobutyl, pentyl, isopentyl, hexyl, isohexyl, heptyl, octyl, nonyl, decyl, etc. Particularly preferred are alkyl groups of about 1 to 6 carbon atoms. Examples of the alkenyl group represented by R² and R³ include groups containing about 3 to 13 carbon atoms such as allyl (2-propenyl), 2-butenyl, 2-pentenyl, 2-hexenyl, 4-propyl-2-pentenyl, cinnamyl, 2-nonyl-2-butenyl, etc. Particularly preferred are alkenyl groups of about 3 to 9 carbon atoms. These alkyl and alkenyl groups may each carry substituent groups in optional substitutable position or positions other than the α-position, and examples of such substituent groups include alkyl groups of about 1 to 4 carbon atoms (e.g. methyl, ethyl, propyl, isopropyl, butyl, isobutyl, sec-butyl, tert-butyl), alkoxy groups of about 1 to 4 carbon atoms (e.g. methoxy, ethoxy, propoxy, iso-propoxy, n-butoxy, iso-butoxy, sec-butoxy, tert-butoxy), alkanoyl groups of about 1 to 4 carbon atoms (e.g. formyl, acetyl, propionyl, n-butyryl, iso-butyryl), hydroxy, nitro, halogen (e.g. fluorine, chlorine, bromine, iodine), cyano, trifluoromethyl, dialkylamino of 2 to 4 carbon atoms (e.g. dimethylamino, diethylamino, dipropylamino, diisopropylamino, dibutylamino), alkanoylamido of 1 to 4 carbon atoms (e.g. formamido, acetamido, propionylamido, butyrylamido, isobutyrylamido) and so on. The preferable number of the substituent groups is one to four.

Examples of the aralkyl group represented by R² or R³ include groups containing about 7 to 12 carbon atoms such as benzyl, phenethyl, 3-phenylpropyl, naphthylmethyl, naphthylethyl, etc. Particularly preferred is benzyl. These aralkyl groups may each carry substituent group or groups in its alkylene moiety other than the α-position and/or its aryl(phenyl) ring, and examples of such substituents include the groups mentioned hereinbefore as examples of the substituent groups of said alkyl and alkenyl groups.

Examples of the cyclic amino group which is formed between R² and R³ taken together with the adjacent nitrogen atom has a methylene group in α-position and include cyclic amino groups of about 5 to 6 members, and each of the cyclic amino groups may contain a second hetero-atom (e.g. N and/or O) in addition to the adjacent nitrogen atom as a ring member. Specific examples of such cyclic amino groups include 1-pyrrolidinyl, 1-pyrrolinyl, 1-imidazolidinyl, 1-imidazolinyl, 1-pyrazolidinyl, 1-pyrazolinyl, morpholino, piperidino, 1-piperazinyl, etc. These cyclic amino groups may each carry substituent group or groups at any position other than the position (α) adjoining to the nitrogen atom, and examples of such substituent groups include the groups mentioned hereinbefore as examples of the substituent groups of said alkyl and alkenyl groups.

The most preferred cases are those when each of $R^2$ and $R^3$ is benzyl or isobutyl.

Examples of the above-mentioned salt of compound (I) include salts with mineral acids such as hydrochloric acid, sulfuric acid, nitric acid, phosphoric acid, boric acid, etc., salts with organic acids such as oxalic acid, tartaric acid, acetic acid, trifluoroacetic acid, methanesulfonic acid, benzenesulfonic acid, p-toluenesulfonic acid, camphorsulfonic acid, etc. and quaternary ammonium salts with methyl bromide, methyl iodide, methyl methanesulfonate, methyl benzenesulfonate, methyl p-toluenesulfonate, etc.

The objective compound (I) or a salt thereof of this invention is produced by subjecting a compound of formula (II)

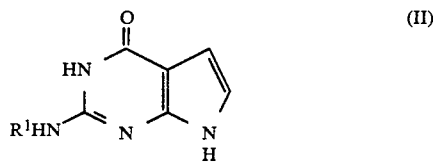

($R^1$ is as defined hereinbefore) and a compound of formula (III)

($R^2$ and $R^3$ are respectively as defined hereinbefore) to Mannich condensation reaction[4] in the presence of a formaldehyde compound.

[4]F. F. Blicke, *Organic Reactions* 1, 303 (1942); H. Hellmann et al., *Angew. Chem.* 68, 265 (1956).

Compound (III) may be used in the form of a salt, examples of which include salts with mineral acids such as hydrochloric acid, sulfuric acid, nitric acid, phosphoric acid, boric acid, etc. and salts with organic acids such as carbonic acid, oxalic acid, tartaric acid, acetic acid, trifluoroacetic acid, methanesulfonic acid, benzenesulfonic acid, p-toluenesulfonic acid, camphorsulfonic acid, etc.

The above-mentioned formaldehyde compound includes reagents which act as the equivalent of formaldehyde in Mannich reaction, such as formaldehyde, paraformaldehyde, formalin, methylal, ethylal, piperidinomethylphthalimide, hexamethylenetetramine, etc.

This Mannich reaction is conducted as follows. Compound (II) or a salt thereof and compound (III) or a salt thereof, in a molar (II)/(III) ratio of about 1 to 1/50, are reacted in the absence or presence of a suitable solvent at a temperature of 0° C. to the boiling point of the reaction solvent, preferably at 20° to 100° C., for about 10 minutes to 48 hours. After the Mannich reaction, the reaction product is then preferably treated with an acid as the final step. The acid treatment gives higher yields of the desired compound.

Examples of the solvent for this Mannich reaction include water, methanol, ethanol, propanol, butanol, pentanol, tetrahydrofuran, dioxane, acetonitrile, pyridine, dimethylformamide, dimethyl sulfoxide, sulfolane, etc. and suitable mixtures of such solvents. The reaction rate and yield can be improved by adjusting and controlling the pH of the reaction system to an optimum pH level (generally, pH 2 to 10) using an acid (e.g. hydrochloric acid, sulfuric acid, phosphoric acid, boric acid, acetic acid, oxalic acid, tartaric acid, trifluoroacetic acid, methanesulfonic acid, benzenesulfonic acid, p-toluenesulfonic acid, camphorsulfonic acid), a base (e.g. sodium hydroxide, potassium hydroxide, lithium hydroxide, barium hydroxide, ammonia, triethylamine) or a salt (e.g. sodium chloride, calcium chloride, sodium carbonate, potassium carbonate, sodium hydrogen carbonate, ammonium chloride). Examples of the acid which is employed in the final step include hydrochloric acid, sulfuric acid, nitric acid, phosphoric acid, boric acid, acetic acid, oxalic acid, tartaric acid, trifluoroacetic acid, methanesulfonic acid, benzenesulfonic acid, p-toluenesulfonic acid, etc. The compound (I) produced in the above manner can be isolated by the conventional separation and purification procedures such as concentration, solvent extraction, recrystallization, chromatography, etc.

The starting material compound (II) employed in accordance with this invention can be easily prepared by the process for production of the known compound (II: $R^1=CH_3CO$)[5] or a process analogous therewith, for example by the process shown below.

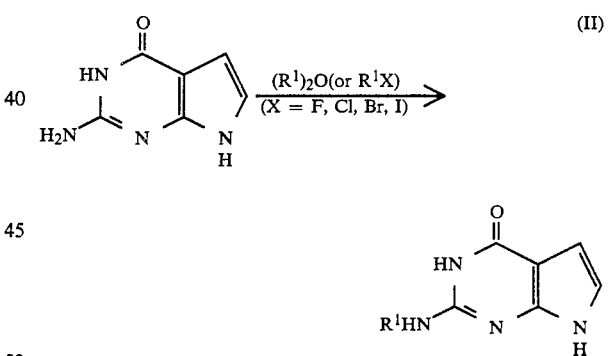

($R^1$ is as defined hereinbefore). Of these compounds (II), the compound wherein $R^1$ is a $C_{4-10}$ alkanoyl or an aroyl group is especially useful for the purposes of this invention.

[5]L. B. Townsend et al., *J. Heterocycl. Chem.*, 76, 13 (1976)

The mating material compound (III) may also be a known compound or a compound prepared by a process analogous to the process for production of the known compound.

The compound (I) or a salt thereof according to this invention can for example be subjected to the following reaction to produce the above-mentioned Q base and its analogs, which are important as biological constituents or as antitumor or other drugs or biological reagents, in high yield and on a commercial scale.

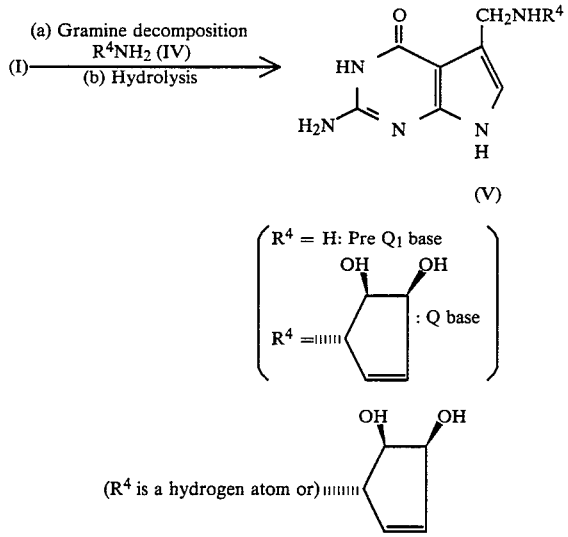

The above gramine decomposition reaction (a)[6] transforms the

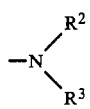

group of compound (I) into —NHR$^4$, and the hydrolysis reaction (b) eliminates the acyl group R$^1$ from compound (I). Either of these reactions may be performed in the first place, and by controlling the conditions for gramine decomposition, it is possible to eliminate the acyl group R$^1$ at the same time to give the desired pre Q$_1$ base or Q base in one operation.

[6] W. J. Houlihan, *Heterocyclic Compounds, Indoles*, Part II, Wiley-Interscience, New York (1972)

The gramine decomposition is effected by reacting a compound (I) or a salt thereof or a deacylated compound thereof with a compound (IV) in the absence or presence of a suitable solvent at a temperature between 0° C. and the boiling point of the solvent, preferably at about 20° to 80° C., for a period of about 10 minutes to 48 hours. If compound (I) is used in the form of a quaternary salt such as salts with methyl bromide, methyl iodide, methyl methanesulfonate, methyl benzenesulfonate, methyl p-toluenesulfonate, etc., the reaction may be conducted under milder conditions. The elimination of R$^1$ may also be effected by continuing to heat the reaction mixture at about 50° to 100° C. after completion of the gramine decomposition.

The hydrolysis reaction is performed in the presence of an ordinary catalyst such as an acid (e.g. a mineral acid such as hydrochloric acid, sulfuric acid, nitric acid, phosphoric acid, etc.), a base (e.g. a metal alkoxide such as sodium methoxide, sodium ethoxide, sodium butoxide, potassium butoxide, etc.; a metal hydroxide such as sodium hydroxide, potassium hydroxide, lithium hydroxide, barium hydroxide, etc.; ammonia) or a salt (e.g. sodium carbonate, potassium carbonate, lithium iodide) in a suitable solvent at a temperature between 0° C. and the boiling point of the solvent, preferably in the range of 10° to 80° C. Examples of the reaction solvent include water, methanol, ethanol, propanol, butanol, tetrahydrofuran, dioxane, pyridine, dimethyl sulfoxide and sulfolane as well as suitable mixtures thereof. This acid hydrolysis reaction may be simultaneously performed at the final stage of acid treatment in the process for production of objective compound (I).

It will be apparent from the foregoing description that by using the new 7-deazapurine derivative or salt thereof according to this invention, Q base and pre Q$_1$ base which heretofore could not be produced on a large scale without considerable difficulties can be produced from inexpensive materials in a short sequence of steps and in high yield.

The following reference and working examples are intended to illustrate this invention in further detail without limiting its scope in any manner. The Rf values indicated in these examples are by silica gel thin layer chromatography (E. Merck, silica gel HPTLC).

The various ratio values of mixtures of solvents are generally expressed in terms of volume/volume or volume/volume/volume. However, the exception to the above general rule is the case with the note of (w/v), which means weight/volume.

REFERENCE EXAMPLE 1

Production of 2-acetaminopyrrolo(2,3-d)pyrimidin-4-one

2-Aminopyrrolo(2,3-d)pyrimidin-4-one (3.0 g) and acetic anhydride (10 g) are suspended in pyridine (50 ml) and the reaction is conducted under reflux for 24 hours. The solvent and excess reagent are distilled off under reduced pressure and, on an ice bath, 5% (W/V) alcoholic ammonia (20 ml) is added to the residue. The mixture is stirred for 2 hours. The resulting crystalline precipitate is collected by filtration and washed with dilute hydrochloric acid and water to give the above-identified compound (2.5 g).

NMR (DMSO-d$_6$/CDCl$_3$, 60 MHz)δ 2.07(s,3H), 6.33(d,1H), 6.73(d,1H).

IR(KBr) ν 1640 cm$^{-1}$.

REFERENCE EXAMPLE 2

Production of 2-n-octanoylaminopyrrolo(2,3-d)pyrimidin-4-one

2-Aminopyrrolo(2,3-d)pyrimidin-4-one (6.0 g) is suspendeed in pyridine (80 ml) and, with stirring on an ice bath, n-octanoyl chloride (22.8 g) is added. The reaction mixture is warmed at 85° C. for 30 minutes and the solvent is distilled off under reduced pressure. Dilute hydrochloric acid is added to the residue and the mixture is extracted with chloroform. The extracts are combined and concentrated to dryness. The residue is dissolved in 8% (W/V) alcoholic ammonia (50 ml) and the solution is allowed to stand at room temperature to give the above-identified compound (8.9 g) as crystals.

NMR (DMSO-d$_6$/D$_2$O, 60 MHz)δ 0.87(1t,3H), 1.30(s,10H), 2.47(t,2H), 6.47(d,1H), 6.80(d,1H).

IR(KBr) ν 1640 cm$^{-1}$.

REFERENCE EXAMPLE 3

Production of 2-(2-ethylhexanoyl)aminopyrrolo(2,3-d)pyrimidin-4-one

Using 2-aminopyrrolo(2,3-d)pyrimidin-4-one and 2-ethylhexanoyl chloride, the above-identified compound is produced by the same procedure as Reference Example 2.

IR(KBr) ν 1655, 1605 cm$^{-1}$.

REFERENCE EXAMPLE 4

Production of 2-undecanoylaminopyrrolo(2,3-d)pyrimidin-4-one

Using 2-aminopyrrolo(2,3-d)pyrimidin-4-one and undecanoyl chloride, the above-identified compound is produced by the same procedure as Reference Example 2.

IR(KBr) $\nu$ 1645 cm$^{-1}$.

REFERENCE EXAMPLE 5

Production of 2-octadecanoylaminopyrrolo(2,3-d)pyrimidin-4-one

Using 2-aminopyrrolo(2,3-d)pyrimidin-4-one and octadecanoyl chloride, the above-identified compound is produced by the same procedure as Reference Example 2.

IR(KBr) $\nu$ 1645 cm$^{-1}$.

REFERENCE EXAMPLE 6

Production of 2-benzoylaminopyrrolo(2,3-d)pyrimidin-4-one

Using 2-aminopyrrolo(2,3-d)pyrimidin-4-one and benzoyl chloride, the above-identified compound is produced by the same procedure as Reference Example 2.

IR(KBr) $\nu$ 1635 cm$^{-1}$.

REFERENCE EXAMPLE 7

Production of 2-cinnamoylaminopyrrolo(2,3-d)pyrimidin-4-one

Using 2-aminopyrrolo(2,3-d)pyrimidin-4-one and cinnamoyl chloride, the above-identified compound is produced by the same procedure as Reference Example 2.

IR(KBr) $\nu$ 1645 cm$^{-1}$.

REFERENCE EXAMPLE 8

Production of 2-(2-naphthoyl)aminopyrrolo(2,3-d)pyrimidin-4-one

Using 2-aminopyrrolo(2,3-d)pyrimidin-4-one and 2-naphthoyl chloride, the above-identified compound is produced by the same procedure as Reference Example 2.

IR(KBr) $\nu$ 1640 cm$^{-1}$.

EXAMPLE 1

Production of 5-N,N-dibenzylaminomethyl-2-n-octanoylaminopyrrolo(2,3-d)pyrimidin-4-one 2-n-Octanoylaminopyrrolo(2,3-d)pyrimidin-4-one (1.67 g) as obtained in Reference Example 2, dibenzylamine (3.6 g) and 30% (W/V) formalin (1.72 g) are dissolved and/or suspended in 80% (W/V) aqueous acetic acid (60 ml) and the reaction is conducted at 60° C. for 20 hours. The solvent and excess reagent are distilled off under reduced pressure. The residue is dissolved by addition of methanol (60 ml) and 1N hydrochloric acid (60 ml), and the solution is allowed to stand at 80° C. for an hour. The resulting mixture is alkalized with ammonia and concentrated to dryness. The residue is diluted with water and extracted with chloroform. The extracts are combined and concentrated to give a crude product, which is recrystallized from ether to give the above-identified compound (2.43 g) as a pure product.

NMR(CDCl$_3$/D$_2$O/DMSO-d$_6$, 60 MHz)$\delta$ 0.90(1t,3H), 1.30(bs, 10H), 2.47(t,2H), 3.80(s,4H), 4.00(s,2H), 6.93(s,1H), 7.33(bs,10H).

IR(KBr) $\nu$ 1645, 1615 cm$^{-1}$.

Rf=0.17 (Developing solvent: chloroform-methanol (7:1)).

EXAMPLE 2

Production of 5-N,N-dibenzylaminomethyl-2-(2-ethylhexanoyl)aminopyrrolo(2,3-d)pyrimidin-4-one Using 2-(2-ethylhexanoyl)aminopyrrolo(2,3-d)pyrimidin-4-one and dibenzylamine, the above-identified compound is produced by the same procedure as Example 1.

NMR(CDCl$_3$, 60 MHz)$\delta$ 0.90(1t,6H), 1.30(bs,8H), 2.57(bs,1H), 3.77(bm,4H), 4.00(bs,2H), 6.90(bs,1H), 7.30(m,10H).

IR(KBr) $\nu$ 1650, 1615 cm$^{-1}$.

Rf=0.15 (Developing solvent: chloroform-ether-methanol (12:4:1)).

EXAMPLE 3

Production of 2-acetamino-5-N,N-dibenzylaminomethylpyrrolo(2,3-d)pyrimidin-4-one Using 2-acetaminopyrrolo(2,3-d)pyrimidin-4-one and dibenzylamine, the above-identified compound is produced by the same procedure as Example 1.

Rf=0.22 (Developing solvent: chloroform-methanol (4:1)).

EXAMPLE 4

Production of 5-N,N-dimethylaminomethyl-2-n-octanoylaminopyrrolo(2,3-d)pyrimidin-4-one Using 2-n-octanoylaminopyrrolo(2,3-d)pyrimidin-4-one and dimethylamine, the above-identified compound is produced by the same procedure as Example 1.

Rf=0.13 (Developing solvent: chloroform-5.8% (w/v) NH$_3$/ethanol (4:1)).

EXAMPLE 5

Production of 5-N,N-diethylaminomethyl-2-n-octanoylaminopyrrolo(2,3-d)pyrimidin-4-one Using 2-n-octanoylaminopyrrolo(2,3-d)pyrimidin-4-one and diethylamine, the above-identified compound is produced by the same procedure as Example 1.

Silica gel thin layer chromatography (HPTLC, E. Merck): Rf=0.35 (Developing solvent: chloroform-methanol (4:1)).

EXAMPLE 6

Production of 2-n-octanoylamino-5-(1-pyrrolidinyl)methylpyrrolo(2,3-d)pyrimidin-4-one Using 2-n-octanoylaminopyrrolo(2,3-d)pyrimidin-4-one and pyrrolidine, the above-identified compound is produced by the same procedure as Example 1.

Rf=0.24 (Developing solvent: chloroform-6.5% (w/v) NH$_3$/ethanol (4:1)).

EXAMPLE 7

Production of 5-N-benzyl-N-methylaminomethyl-2-n-octanoylaminopyrrolo(2,3-d)pyrimidin-4-one Using 2-n-octanoylaminopyrrolo(2,3-d)pyrimidin-4-one (1.38 g) and benzylmethylamine (1.82 g), the above-identified compound (105 mg) is produced by the same procedure as Example 1.

Rf=0.38 (Developing solvent: chloroform-methanol (4:1)).

EXAMPLE 8

Production of 5-N,N-dibenzylaminomethyl-2-benzoylaminopyrrolo(2,3-d)pyrimidin-4-one Using 2-benzoylaminopyrrolo(2,3-d)pyrimidin-4-one and benzylamine, the above-identified compound is produced by the same procedure as Example 1.

Rf=0.35 (Developing solvent: chloroform-methanol (4:1)).

EXAMPLE 9

Production of 2-n-octanoylamino-5-(4-methyl-1-piperazinyl)methylpyrrolo(2,3-d)pyrimidin-4-one Using 2-n-octanoylaminopyrrolo(2,3-d)pyrimidin-4-one and N-methylpiperazine, the above-identified compound is produced by the same procedure as Example 1.

Rf=0.30 (Developing solvent: chloroform-methanol (4:1)).

EXAMPLE 10

Production of 5-N,N-di(m-methylbenzyl)aminomethyl-2-n-octanoylaminopyrrolo(2,3-d)pyrimidin-4-one Using 2-n-octanoylaminopyrrolo(2,3-d)pyrimidin-4-one and di(m-methylbenzyl)amine, the above-identified compound is produced by the same procedure as Example 1.

Rf=0.40 (Developing solvent: chloroform-methanol (4:1)).

EXAMPLE 11

Production of 5-N,N-di(p-methoxybenzyl)aminomethyl-2-n-octanoylaminopyrrolo(2,3-d)pyrimidin-4-one Using 2-n-octanoylaminopyrrolo(2,3-d)pyrimidin-4-one and di(p-methoxybenzyl)amine, the above-identified compound is produced by the same procedure as Example 1.

Rf=0.38 (Developing solvent: chloroform-methanol (4:1)).

EXAMPLE 12

Production of 5-N,N-diallylaminomethyl-2-n-octanoylaminopyrrolo(2,3-d)pyrimidin-4-one Using 2-n-octanoylaminopyrrolo(2,3-d)pyrimidin-4-one and diallylamine, the above-identified compound is produced by the same procedure as Example 1.

Rf=0.12 (Developing solvent: chloroform-methanol (7:1)).

EXAMPLE 13

Production of 5-N,N-diisobutylaminoethyl-2-n-octanoylaminopyrrolo(2,3-d)pyrimidin-4-one Using 2-n-octanoylaminopyrrolo(2,3-d)pyrimidin-4-one and diisobutylamine, the above-identified compound is produced by the same procedure as Example 1.

Rf=0.23 (Developing solvent: chloroform-methanol (7:1)).

REFERENCE EXAMPLE 9

Production of 2-amino-5-N,N-dibenzylaminomethylpyrrolo(2,3-d)pyrimidin-4-one

5-N,N-Dibenzylaminomethyl-2-n-octanoylaminopyrrolo(2,3-d)pyrimidin-4-one (971 mg) as obtained in Example 1 is dissolved in methanol-tetrahydrofuran (1:1, 60 ml) and, following addition of 5N KOH (2.5 ml), the mixture is stirred at room temperature for 60 hours. The solvent is then distilled off under reduced pressure and the residue is column-chromatographed on silica gel (Kiesel gel 60, product distributed by E. Merck) and on ion-exchange resin (IRA-68, product distributed by Rohm & Haas Co.) to give the above-identified compound (601 mg).

The developing solvent for silica gel and the ion-exchange resin are 5% (w/v) $NH_3/CH_3OH:CHCl_3 = 1:9$ and 50% aqueous methanol, respectively.

NMR ($CDCl_3/DMSO-d_6$, 60 MHz)$\delta$ 3.63(s,4H), 3.83(s,2H), 5.87(bs,2H), 6.60(bs,1H), 7.20(m,10H).

IR(KBr) $\nu$ 1665, 1625, 1600 cm$^{-1}$.

Rf=0.35 (Developing solvent: chloroform-methanol (4:1)).

REFERENCE EXAMPLE 10

Using the compounds of Examples 2 and 8 and following the procedure of Reference Example 9, there is obtained the compound of Reference Example 9.

REFERENCE EXAMPLE 11

Following the procedure of Reference Example 9, there are obtained the following compounds:

2-Amino-5-N,N-diethylaminomethylpyrrolo(2,3-d)pyrimidin-4-one, Rf=0.20;

2-Amino-5-pyrrolidinomethylpyrrolo(2,3-d)pyrimidin-4-one, Rf=0.21;

2-Amino-5-N-benzyl-N-methylaminomethylpyrrolo(2,3-d)pyrimidin-4-one, Rf=0.19;

2-Amino-5-N-methylpiperazinomethylpyrrolo(2,3-d)pyrimidin-4-one, Rf=0.17;

2-Amino-5-N,N-di(m-methylbenzyl)aminomethylpyrrolo(2,3-d)pyrimidin-4-one, Rf=0.38;

2-Amino-5-N,N-di(p-methoxybenzyl)aminomethylpyrrolo(2,3-d)pyrimidin-4-one, Rf=0.36.

In all the above cases, the developing solvent is chloroform-methanol (4:1).

REFERENCE EXAMPLE 12

Production of 2-amino-5-((3S,4R,5S)-4,5-dihydroxycyclopent-1-en-3-ylaminomethyl)pyrrolo(2,3-d)pyrimidin-4-one (Q base)

2-Amino-5-N,N-dibenzylaminomethylpyrrolo(2,3-d)pyrimidin-4-one (359 mg) as obtained in Reference Example 9 and (3S,4R,5S)-4,5-O-isopropylidene-4,5-dihydroxycyclopent-1-en-3-ylamine (310 mg) are dissolved in methanol and the reaction is conducted in a sealed tube at 60° C. for 24 hours. An equal volume of 1N hydrochloric acid is added and the mixture is warmed again at 70° C. for an hour. The solvent is then distilled off under reduced pressure and the residue is column-chromatographed on cellulose powder (Cellulose Powder B, product distributed by Toyo Roshi Co. in Japan) and ion-exchange resin (IRA-68) to give the above-identified compound (65 mg).

The developing solvents for cellulose powder and the ion exchange resin are n-butanol saturated with concd. aqueous ammonia and water, respectively. Physicochemical characteristics are measured after conversion to the hydrochloride by treatment with methanolic hydrochloric acid.

NMR (D$_2$O, 60 MHz)δ 4.28–4.60(m,2H), 4.50(bs,2H), 6.13(dd, 1H), 6.35(m,1H), 7.12(s,1H).

mp 230°–235° C. (decomp.).

IR(KBr) ν 3300, 3100, 2950, 2770, 1675, 1610 cm$^{-1}$.

REFERENCE EXAMPLE 13

Production of 2-amino-5-aminomethylpyrrolo(2,3-d)pyrimidin-4-one (Pre Q$_1$ base)

2-Amino-5-N,N-dibenzylaminomethylpyrrolo(2,3-d)pyrimidin-4-one (320 mg) as obtained in Reference Example 9 is dissolved in a mixture of 5% (W/V) alcoholic ammonia (15 ml) and aqueous ammonia (15 ml) and the reaction is conducted in a sealed tube at 45° C. for 17 hours. After cooling, the solvent is distilled off under reduced pressure and the residue is column-chromatographed on cellulose powder (Cellulose Powder B) and ion-exchange resin (CG-50, product distributed by Rohm & Haas Co.) to give the above-identified compound (120 mg).

The developing solvent for Cellulose Powder B is the same as that used in the reference example 12. The developing solvent for the ion-exchange resin is water and an aqueous ammonia.

Physico-chemical characteristics are measured after conversion to the hydrochloride by treatment with methanolic hydrochloric acid.

NMR (CD$_3$OD/D$_2$O, 60 MHz)δ 4.32(s,2H), 7.12(s,1H).

IR(KBr) ν 3100, 1670, 1605, 1050 cm$^{-1}$.

mp 220°–225° C. (decomp.)

UVλ$_{max}^{MeOH}$ 217, 260, 281 nm.

REFERENCE EXAMPLE 14

Using any of 2-amino-5-N,N-diethylaminomethylpyrrolo(2,3-d)pyrimidin-4-one, 2-amino-5-(1-pyrrolidinyl)methylpyrrolo(2,3-d)pyrimidin-4-one, 2-amino-5-N-benzyl-N-methylaminomethylpyrrolo(2,3-d)pyrimidin-4-one, 2-amino-5-(4-methyl-1-piperazinyl)methylpyrrolo(2,3-d)pyrimidin-4-one, 2-amino-5-N,N-di(m-methylbenzyl)aminomethylpyrrolo(2,3-d)pyrimidin-4-one and 2-amino-5-N,N-di(p-methoxybenzyl)aminomethylpyrrolo(2,3-d)pyrimidin-4-one and following the procedure of Reference Example 12 or 13, there is obtained the corresponding Q base or pre Q$_1$ base.

REFERENCE EXAMPLE 15

Production of 2-amino-5-aminomethylpyrrolo(2,3-d)pyrimidin-4-one (Pre Q$_1$ base)

5-N,N-Dimethylaminomethyl-2-n-octanoylaminopyrrolo(2,3-d)pyrimidin-4-one (157 mg) is dissolved in a mixture of alcohol (25 ml) and aqueous ammonia (8 ml) and the reaction is conducted in a sealed tube at 75° C. for 15 hours. After cooling, a small amount of the insoluble matter is filtered off and the filtrate is concentrated to dryness to give a crude product, which is column-chromatographed on cellulose powder and ion-exchange resin (IRA-68) to give the above-identified compound (56 mg).

Physico-chemical characteristics are in complete agreement with those of the compound obtained in Reference Example 13.

REFERENCE EXAMPLE 16

Using any of 2-acetamino-5-N,N-dibenzylaminomethylpyrrolo(2,3-d)pyrimidin-4-one, 5-N,N-diallylaminomethyl-2-n-octanoylaminopyrrolo(2,3-d)pyrimidin-4-one and 5-N,N-diisobutylaminomethyl-2-n-octanoylaminopyrrolo(2,3-d)pyrimidin-4-one and following the procedure of Reference Example 15, there is obtained the corresponding pre Q$_1$ base.

In the above Examples and Reference Examples, alcoholic ammonia means NH$_3$ in C$_2$H$_5$OH.

What is claimed is:

1. A 7-deazapurine compound of the formula:

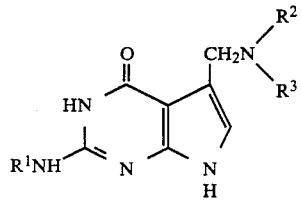

wherein R$^1$ is an alkanoyl group having 1 to 18 carbon atoms, a benzoyl, toluoyl, naphthoyl, phenylacetyl, or cinnamoyl group, each of R$^2$ and R$^3$ is an alkyl group of 1 to 10 carbon atoms, alkenyl group of 3 to 13 carbon atoms or an aralkyl group of the class consisting of benzyl, phenethyl, phenylpropyl, naphthylmethyl, and naphthylethyl, or wherein NR$^2$R$^3$ forms a cyclic amino group of the class consisting of 1-pyrrolidinyl, 1-pyrrolinyl, 1-imidazolidinyl, 1-imidazolinyl, 1-pyrazolidinyl, 1-pyrazolinyl, morpholino, piperidino, and 1-piperazinyl, and wherein the said alkyl group, alkenyl group, aralkyl group and cyclic amino group may have at a position or positions other than the α-position one to four substituents selected from the group consisting of an alkyl group of 1 to 4 carbon atoms, an alkoxy group of 1 to 4 carbon atoms, an alkanoyl group of 1 to 4 carbon atoms, hydroxy, nitro, halogen, cyano, trifluoromethyl, a dialkylamino group of 2 to 8 carbon atoms, and an alkanoylamido group of 1 to 4 carbon atoms, or a pharmaceutically acceptable salt thereof.

2. A 7-deazapurine compound as claimed in claim 1, wherein R$^1$ is an alkanoyl group of 4 to 10 carbon atoms or benzoyl and each of R$^2$ and R$^3$ is benzyl or isobutyl.

3. A 7-deazapurine compound as claimed in claim 1, wherein R$^1$ is n-octanoyl and each of R$^2$ and R$^3$ is benzyl.

4. A 7-deazapurine compound as claimed in claim 1, wherein R$^1$ is benzoyl and each of R$^2$ and R$^3$ is benzyl.

5. A 7-deazapurine compound as claimed in claim 1, wherein $R^1$ is n-octanoyl and each of $R^2$ and $R^3$ is isobutyl.

6. A method of producing 7-deazapurine compound of the formula:

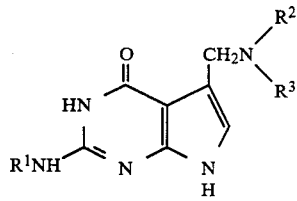

wherein $R^1$ is an alkanoyl group having 1 to 18 carbon atoms, a benzoyl, toluoyl, naphthoyl, phenylacetyl, or cinnamoyl group, each of $R^2$ and $R^3$ is an alkyl group of 1 to 10 carbon atoms, alkenyl group of 3 to 13 carbon atoms or an aralkyl group of the class consisting of benzyl, phenethyl, phenylpropyl, naphthylmethyl, and naphthylethyl, or wherein $NR^2R^3$ forms a cyclic amino group of the class consisting of 1-pyrrolidinyl, 1-pyrrolinyl, 1-imidazolidinyl, 1-imidazolinyl, 1-pyrazolidinyl, 1-pyrazolinyl, morpholino, piperidino, and 1-piperazinyl, and wherein the said alkyl group, alkenyl group, aralkyl group and cyclic amino group may have at a position or positions other than the α-position one to four substituents selected from the group consisting of an alkyl group of 1 to 4 carbon atoms, an alkoxy group of 1 to 4 carbon atoms, an alkanoyl group of 1 to 4 carbon atoms, hydroxy, nitro, halogen, cyano, trifluoromethyl, a dialkylamino group of 2 to 8 carbon atoms and an alkanoylamido group of 1 to 4 carbon atoms, or a pharmaceutically acceptable salt thereof, which comprises subjecting a compound of the formula

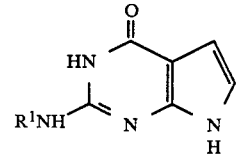

wherein $R^1$ has the same meaning as defined above, and a compound of the formula:

wherein $R^2$ and $R^3$ have the same meaning as defined above, to Mannich condensation reaction in the presence of a formaldehyde compound.

7. A method as claimed in claim 6, wherein $R^1$ is n-octanoyl or benzoyl and each of $R^2$ and $R^3$ is benzyl or isobutyl.

8. A method as claimed in claim 6, wherein a formaldehyde compound is formaldehyde.

* * * * *